United States Patent [19]

Tanaka

[11] Patent Number: 4,966,205
[45] Date of Patent: Oct. 30, 1990

[54] METHOD AND APPARATUS FOR CHARGING TRANSPARENT MATERIAL

[75] Inventor: Yoshinori Tanaka, Shizuoka, Japan

[73] Assignee: Pola Chemical Industries Ltd., Shizuoka, Japan

[21] Appl. No.: 284,436

[22] Filed: Dec. 14, 1988

[30] Foreign Application Priority Data

Feb. 2, 1988 [JP] Japan .................. 63-22573

[51] Int. Cl.⁵ .................. A61K 7/00; B65B 3/04
[52] U.S. Cl. .................. 141/9; 141/104; 141/105; 141/255; 141/270; 141/284; 239/214.25; 239/226; 239/227
[58] Field of Search ............ 141/1, 2, 9, 18, 100, 141/101, 104, 105, 106, 107, 250, 253, 255, 257, 258, 260, 262, 263, 270, 275, 276, 284; 239/97, 98, 214.25, 226, 227

[56] References Cited

U.S. PATENT DOCUMENTS

| | | | |
|---|---|---|---|
| 1,951,694 | 3/1974 | Goulstone | 141/100 X |
| 2,107,987 | 2/1938 | Johnson | 141/255 X |
| 3,219,673 | 4/1964 | Stanley et al. | 141/100 X |
| 3,267,971 | 8/1966 | Mueller | 141/9 |
| 3,347,287 | 10/1967 | Geber | 141/105 |
| 3,479,429 | 11/1969 | Morshauser et al. | |
| 3,509,920 | 5/1970 | Word | 141/100 |
| 3,886,973 | 6/1975 | Kinney | 141/105 |
| 3,952,782 | 4/1976 | Mannara | 141/100 |
| 4,159,028 | 6/1979 | Barker et al. | 141/9 |

FOREIGN PATENT DOCUMENTS

| | | |
|---|---|---|
| 19997 | 7/1970 | Japan . |
| 59-225108 | 12/1984 | Japan . |
| 1486634 | 9/1977 | United Kingdom . |

Primary Examiner—Ernest G. Cusick
Attorney, Agent, or Firm—Oliff & Berridge

[57] ABSTRACT

The present invention relates to a method and apparatus for charging a cosmetic material which is capable of providing a transparent cosmetic material containing a three-dimensional pattern formed by a coloring material. Method and apparatus are provided for charging a transparent gel base as well as a coloring material into a charging nozzle and injecting the transparent gel base and coloring material from the tip of the charging nozzle into a vessel. The vessel can be rotated and at least one of the vessel and charging nozzle can be moved in longitudinal directions.

7 Claims, 6 Drawing Sheets

CHANGE IN ROTATIONAL SPEED    LOW ——————————— HIGH

THE DIAMETER OF THE CHARGING NOZZLE WAS CHANGED WITH THE DIAMETER OF THE SUB-NOZZLE BEING CONSTANT

THIN ─────────────────── THICK
(LOW ROTATIONAL SPEED)           (HIGH ROTATIONAL SPEED)

CHARGING SPEED

LOW ——————————— HIGH (a)

METHOD AND APPARATUS FOR CHARGING TRANSPARENT MATERIAL

BACKGROUND OF THE INVENTION

The present invention relates to a method of charging a transparent cosmetic material containing a three-dimensional pattern, a nozzle used for charging the material and an apparatus for charging the same which is provided with such a nozzle.

Cosmetic materials generally contain various types of coloring materials such as pigments and dyes. Such coloring materials are in some cases contained as masking agents for covering coloring derived from raw materials and are in some cases contained for the purpose of providing a particular effect in relation to skin make-up which is a positive function of those coloring materials.

Since consumers have recently shown an increasingly diverse sense of appreciation in regard to the value of cosmetic materials, however, cosmetic materials of this kind are now required to possess certain additional merits related to their intrinsic appeal as objects of beauty which provide pleasure in use, as well as their basic functions of being suitable for make-up and so forth.

The inventors therefore conceived the idea of making a main cosmetic material transparent and of forming a three-dimensional pattern in the transparent cosmetic material by using coloring materials.

The method of producing a multicolored rod-shaped cosmetic material described in Japanese Patent Laid-Open No. 225108/1984 is a known method of charging cosmetic materials of different colors for the purpose of allowing a color pattern to be formed by suitably mixing these cosmetic materials.

In the method described in this publication, however, basic raw materials of each of the colors mixed and melted in each of two mixing tanks is directly charged into a mold used for molding a rod-shaped cosmetic material which is rotatably disposed below each of the mixing tanks with a pipe connected to each mixing tank at its upper end. Since the two basic raw materials are simply combined in the pipes and then charged in the mold, a scroll is only formed on the surface of a molded rod-shaped cosmetic material The formation of a three-dimensional pattern cannot therefore be achieved even by this method.

SUMMARY OF THE INVENTION

The present invention has been achieved in consideration of the above-described problem of the prior art, and it is a technical object of the present invention to provide a method of charging a cosmetic material which is capable of providing a transparent cosmetic material containing a three-dimensional pattern formed by a coloring material, and another object of the present invention is to provide a multiple charging nozzle and charging apparatus which are suitable for charging such a cosmetic material.

The method of the present invention is a charging method in which a coloring material is charged into a vessel at the same time as a transparent gel base comprising a water soluble polymer or inorganic gelatinizer is charged into the vessel so as to form a three-dimensional pattern in the transparent gel base using this coloring material. and in which the transparent gel base is introduced into a charging nozzle from the supply source of the transparent gel base, the coloring material also being introduced from the supply source of the coloring material being joined to the gel base in the charging nozzle. and the transparent gel base and the coloring material injected from the tip of the charging nozzle being received by a vessel while at least one of the vessel and the charging nozzle is moved in directions X, Y and Z which intersect each other at right angles.

The kind of charging nozzle which is optimal for use in the charging method of the present invention is a multiple charging nozzle comprising a charging nozzle for injecting the transparent gel base and at least one sub-nozzle for supplying the coloring material, the sub-nozzle being contained in the charging nozzle. The charging apparatus of the present invention is an apparatus in which the multiple charging nozzle is moved (as well as being rotated) in the directions X, Y and Z relative to the charging vessel.

BRIEF DESCRIPTION OF THE DRAWINGS

FIGS. 3(a) to 3(e) are drawings of the change which takes place in a pattern with a change in the distance between the multiple charging nozzle and the surface of the charged liquid;

FIGS. 5(a) to 5(f) are drawings of the change which takes place in a pattern as the diameter of a charging nozzle is changed with the diameter of a sub-nozzle being kept constant, in which FIGS. 5(a) and 5(b) are front views, FIGS. 5(c) and 5(d) are plan views and FIGS. 5(e) and 5(f) are sectional views of the cosmetic materials injected from the multiple charging nozzle;

FIGS. 8(a) and 8(b) to FIGS. 14(a) and 14(b) are plan views and front views of examples of the present invention.

DESCRIPTION OF PREFERRED EMBODIMENTS OF THE INVENTION

In the present invention, coloring materials join linearly a transparent gel base comprising a main cosmetic material, and one or both of a charging nozzle and a vessel are moved in directions X, Y and Z during charging of these materials so that a three-dimensional pattern having any desired configuration can be formed in the transparent gel base by using the linear coloring materials within the range within which the vessel and the nozzle can be moved.

The transparent gel base comprises a water soluble polymer which exhibits a higher level of viscosity than a given value when the polymer is dissolved in water or is produced by neutralization with an alkali or acid. Examples of such polymers include cellulose derivatives such as methyl cellulose, hydroxyethyl cellulose, hydroxypropyl cellulose and carboxymethyl cellulose; natural polymers such as sodium alginate, carageenan, Queen's seed gum and xanthane gum; and synthetic polymers such as polyvinyl alcohol, carboxyvinyl polymers, polyacrylic soda and polyacrylic glycerin ester.

Magnesium silicate may be used as an inorganic gelatinizer.

When such a water-soluble polymer or inorganic gelatinizer is dissolved in water to form a transparent gel base, the viscosity is preferably 15,000 centipoise (referred to as "CP" hereinafter) or more, more preferably 25,000 CP or more, so that stability of the coloring material can be maintained. The upper limit of the viscosity is not necessarily restricted so long as the transparent gel base is capable of being charged properly.

One possible form of charging with at least one of the vessel and the charging nozzle being moved in directions X, Y, Z which intersect each other at right angles is an arrangement in which the vessel is rotated in the plane XY and at least one of the vessel and the charging nozzle is moved in the direction of the Z axis so that they do not coincide with each other when the transparent gel base and the coloring material which are both injected from the tip of the charging nozzle are received by the vessel.

Since the various water soluble polymers mentioned above show different viscosity characteristics during dissolution in water, they may be appropriately prepared by controlling the concentration or by mixing two or more water-soluble polymers.

The transparent gel base may contain various water-soluble components such as polyhydric alcohols, sugars, polysaccharides, amino acid, antioxidants, preservatives and the like, in accordance with the purpose.

Any type of coloring material such as liquid crystals and other pigments, dyes and emulsions can generally be used as the coloring material in the present invention, so long as a pattern can be formed in the transparent gel base.

Examples of liquid crystals include (1) cholesteryl esters such as cholesteryl pelargonate, cholesteryl benzoate, cholesteryl cinnamate, cholesteryl adipate, cholesteryl p-nitrobenzoate, cholesteryl 3,4-dinitrobenzoate, cholesteryl 2-ethylhexanoate and the like; (2) cholesteryl carbonate esters such as cholesteryl cetylcarbonate, cholesteryl ethylcarbonate, cholesteryl methylcarbonate, cholesteryl oleylcarbonate, cholesteryl isostearylcarbonate, cholesteryl 2-methoxyethylcarbonate, cholesteryl propargylcarbonate and the like; (3) cholesteryl halides such as cholesteryl chloride, cholesteryl bromide, cholesteryl ionide and the like; and (4) others such as p-azoxyphenetole, p-methoxycinnamic acid and sodium oleate.

Examples of pigments and dyes include inorganic pigments such as yellow iron oxide, red iron oxide, ultramarine blue pigment, chromium oxide, titanium oxide and mica; tar dyestuffs such as Red No. 2, Red No. 204, Red No. 205, Red No. 219, Blue No. 1, Yellow No. 4 and Yellow No. 204; and natural dyestuffs such as laccaic acid, carminic acid and brazilin.

Of these coloring materials, for example, the inorganic pigments and Red No. 204 which are both water-insoluble are used as they are or preferably after they have been subjected to water repellent treatment with silicone oil, and Red No. 2, Blue No. 1 and laccaic acid which are all water soluble are used after being subjected to water repellent treatment.

Examples of emulsions that may be used in the present invention include water-in-oil type emulsions, oil-in-water type emulsions and water/oil/water type emulsions, but water-in-oil type emulsions are preferable from the viewpoints of the formation of a beautiful pattern and stability during passage of a long time.

Each of these emulsions comprises at least (1) and (3) of following (1) to (4) components: (1) an oil phase component which is appropriately selected from the group consisting of hydrocarbons, triglycerides, higher esters, higher alcohols, higher fatty acids, silicone oil and the like; (2) an oil-soluble additive component which is appropriately selected from the group consisting of antioxidants, ultraviolet absorbing agents, preservatives, surfactants and the like; (3) a water phase component which is appropriately selected from the group consisting of polyhydric alcohols. humectants and the like; and (4) a water-soluble additive component which is appropriately selected from the group consisting of water-soluble vitamins, amino acids, sugars such as monosaccharides and polysaccharides. and preservatives. These components are generally used in cosmetic materials.

Of the above-described emulsions, a water-in-oil type emulsion is produced by selecting an oil phase component and a water phase component in accordance with the use of the cosmetic material, adding under agitation the water phase component which is melted by heating and mixed to the oil phase component which is also melted by heating and mixed, and then cooling the obtained mixture. The water-in-oil type emulsion is intrinsically useful as a cosmetic material for cold cream or hand cream.

The ratio of the oil phase component to the water-in-oil type emulsion is 5 to 70% by weight. The water-in-oil type emulsion itself has a milky color and can be thus used as a coloring material, but this may be colored with a coloring agent for the purpose of increasing the apparent beauty of the cosmetic material. Examples of coloring agents include coloring agents like inorganic pigments such as yellow iron oxide, red iron oxide, ultramarine blue pigment, chromium oxide, titanium oxide and mica titanium; tar dyestuffs such as Red No. 204, Red No. 205 and Blue No. 1; natural dyestuffs such as laccaic acid, carminic acid and guaiazulene; and coloring agents obtained by coloring synthetic resin such as polyethylene and polyethylene terephthalate.

These coloring agents are used as they are or after they have been subjected to water repellent treatment with silicone oil. The amount of the coloring agent added depends upon the intended form and the kind of the coloring agent used, but it is approximately within the range of 0.001% by weight to 30% by weight of the whole of the water-in-oil type emulsion. The coloring agent to be used can be appropriately prepared by mixing two or more of the above-described coloring agents.

An oil-in-water type emulsion is produced by adding a water phase component to an oil phase component by the same method as with the water-in-oil emulsion, followed by inversion, and this emulsion itself is useful as nourishing cream or milky lotion. When this emulsion is used as a coloring material, it can be used singly or in combination with a coloring agent in the same way as the water-in-oil type emulsion.

A water/oil/water type emulsion is obtained by adding a water-in-oil type emulsion to a water phase component, is intrinsically useful as nourishing cream and can be used as a coloring material singly or in combination with a coloring agent.

The amount of the coloring material mixed in the transparent gel base is preferably 0.001 to 20% by weight. With an amount less than 0.001% by weight, no pattern can be formed, while, with an amount over 20% by weight, the coloring material coagulates and thus brings about a feeling of incompatibility with the transparent gel base during application.

When the coloring material is used, it may be mixed in the transparent gel base and charged from a sub-nozzle.

Figure 1:
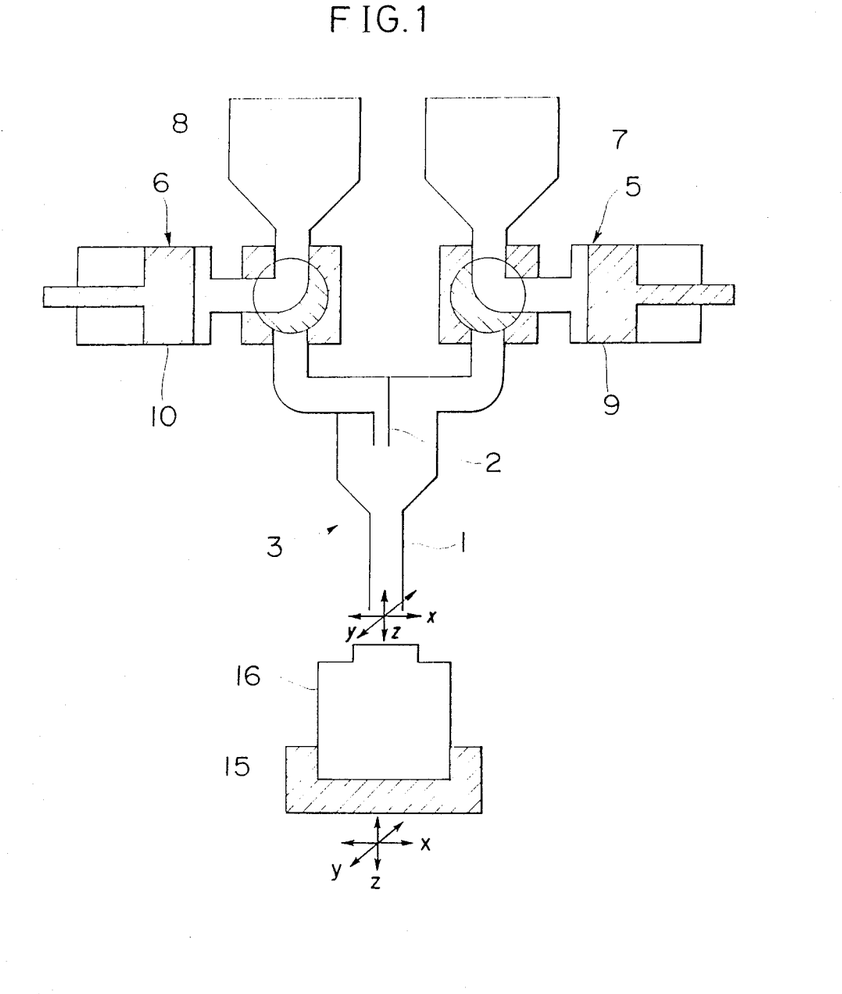
FIG. 1 is a drawing of an example of a charging apparatus for use in a charging method of the present invention.
Figure 2A:
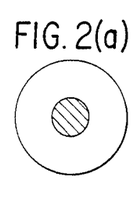
FIGS. 2(a) to 2(g) are sectional views of cosmetic materials which are injected from a multiple charging nozzle.
Figure 2B:
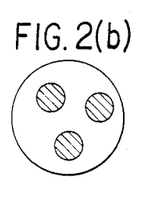
Figure 2C:
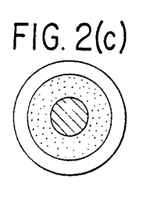
Figure 2D:
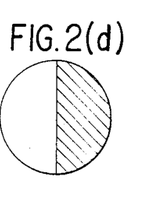
Figure 2E:
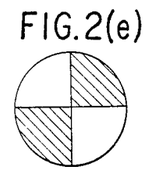
Figure 2F:
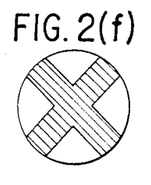
Figure 2G:
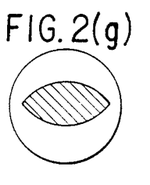

As shown in FIG. 1, an apparatus optimal for performing the method of the present invention is provided with a multiple charging nozzle 3 comprising a charging nozzle 1 for injecting the transparent gel base and at least one sub-nozzle 2 for supplying the coloring material, the sub-nozzle 2 being contained in the charging nozzle 1.

The cosmetic material can be injected with various sectional forms, for example, the forms shown in FIGS. 2(a) to 2(g), by changing the number of sub-nozzles 2, the sectional form thereof and the position thereof in the charging nozzle 1. In FIG. 2. shadowed portions each denote the coloring material, and particularly in FIG. 2(c), the sub-nozzle 2 has a double form so that the coloring material is injected from the inner side and a semi-transparent cosmetic material is injected from the outer side.

If the multiple charging nozzle 3 is so formed as to be rotatable or only the charging nozzle 1 of the multiple charging nozzle 3 is so formed as to be rotatable and if the outlet end of the sub-nozzle 2 is positioned eccentrically to the axis of the charging nozzle 1. since the coloring material forms a linear helical pattern during injection, a three-dimensional pattern can be formed by this linear helical pattern.

In the multiple charging nozzle 3, as shown in FIG. 1, the charging nozzle 1 is connected to one charger 5, and the sub-nozzle 2 is connected to the other charger 6 so that the transparent gel base and the coloring material are forced into the charging nozzle 1 and the sub-nozzle 2 from hoppers 7, 8 by piston cylinders 9, 10, respectively.

A vessel holder 15 for holding a vessel is provided below the multiple charging nozzle 3 in such a manner that one or both of the vessel holder 15 and the multiple charging nozzle 3 can be moved in directions X, Y, Z by means of a driving apparatus (not shown).

In this case, for example, when the charging is performed by using the multiple charging nozzle 3 which is held between robot arms serving as the driving apparatus and which is moved in the directions X, Y, Z by control using a microcomputer in accordance with a given program, a three-dimensional pattern is formed in the transparent gel base by the coloring material in accordance with the locus of the movement.

Alternatively, a rotational driving means for rotating the vessel holder 15 and a longitudinal driving means for longitudinally driving the vessel holder 15 are provided as the driving apparatus so that the vessel holder 15 can be rotated in the XY plane and moved in the Z-axis direction, i.e, in the longitudinal direction, and, during charging, the vessel 16 is first raised so that the tip of the multiple charging nozzle 3 enters the vessel 16, and then rotated, as well as being downwardly moved, whereby a three-dimensional pattern can be formed. In this case, since the cosmetic material discharged in the vessel 16 from the nozzle 3 is piled up along the internal wall of the vessel 16 owing to the centrifugal force, if the vessel 16 has a cylindrical form, a three-dimensional pattern having a coil-like form is formed by the coloring material.

A description will now be given of various forms of the charging method in this case.

The effect of the distance between the tip of the nozzle and the surface of the charged material on the three-dimensional pattern formed is first considered. As shown in FIGS. 3(a) to 3(e), when the tip of the nozzle is brought into contact with or very close to the surface of the charged material, a uniform coil-shaped pattern is formed, and, when the distance becomes large, a non uniform pattern having such a particular feeling that a coil is divided is formed.

Figure 4:
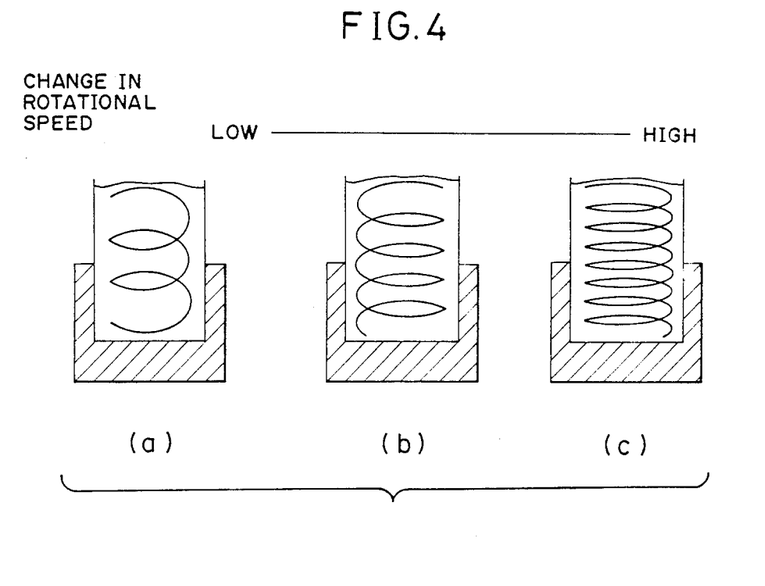
FIGS. 4(a) to 4(c) are drawings of the change which takes place in a pattern with a change in the rotational speed of a vessel.

As shown in FIGS. 4(a) to 4(c), the pattern formed also depends upon the rotational speed of the vessel. At a higher rotational speed, the line formed is thin as viewed from the side of the vessel, and the number of turns of a coil is large, as well as the pattern formed being closer to the internal wall of the vessel owing to the centrifugal force.

Figure 5:
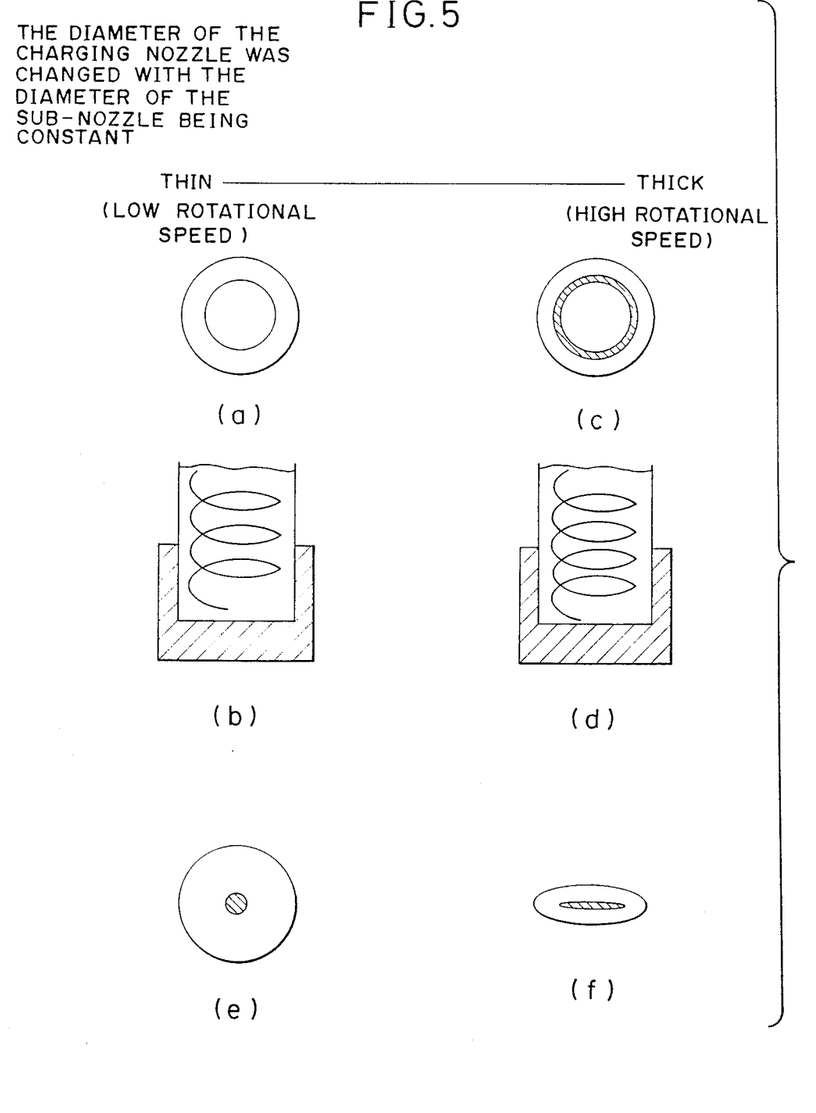

As shown in FIG. 5(a) to 5(f), when the diameter of the charging nozzle 1 is changed without the diameter of the sub-nozzle 2 being changed, in the case of a small diameter of the charging nozzle 1, the pattern formed by the coloring material has the circular cross-sectional form shown in FIG. 5(e), while, in the case of a large diameter of the charging nozzle 1, the pattern has the squeezed flat cross-sectional form shown in FIG. 5(f) and becomes thick as viewed from a plane. When the rotational speed of the vessel is changed without the diameter of the sub-nozzle 2 being changed, the line of the pattern formed is thick as viewed from a plane.

Figure 6:
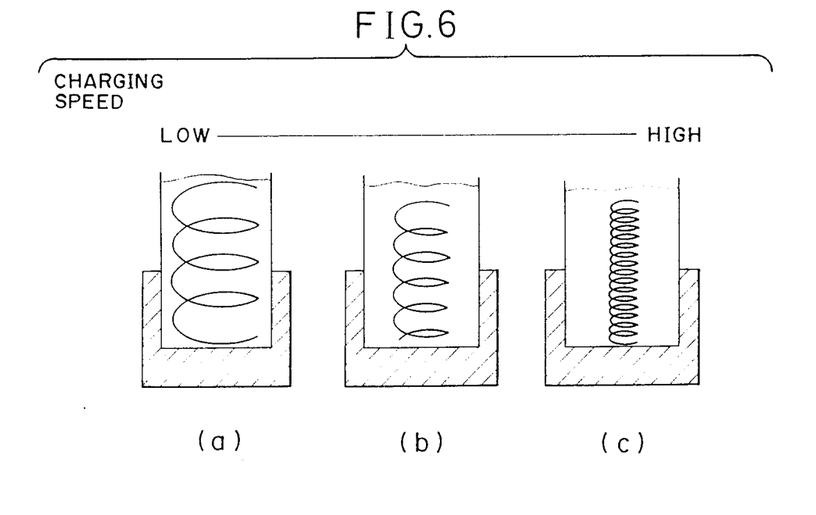
FIGS. 6(a) to 6(c) are drawings of the change which takes place in a pattern with a change in the charging speed of a cosmetic material.

As shown in FIGS. 6(a) to 6(c), at a high charging speed, the diameter of the coil formed becomes small, and at a low charging speed, the diameter of the coil formed becomes large.

Although not shown in the drawings, if the charging nozzle is stepwisely displaced during the rotation of the vessel, a coil-shaped pattern having diameters which vary in a stepwise manner or a disordered pattern can be formed.

In the case of charging by rotation of the vessel the pattern formed also depends upon the shape of the vessel. For example, in the case of a cylindrical vessel, the pattern formed has a circular coil like shape, and in the case of a triangle cylindrical vessel, the pattern formed has a triangle coil-like shape.

Figures 3, 7:
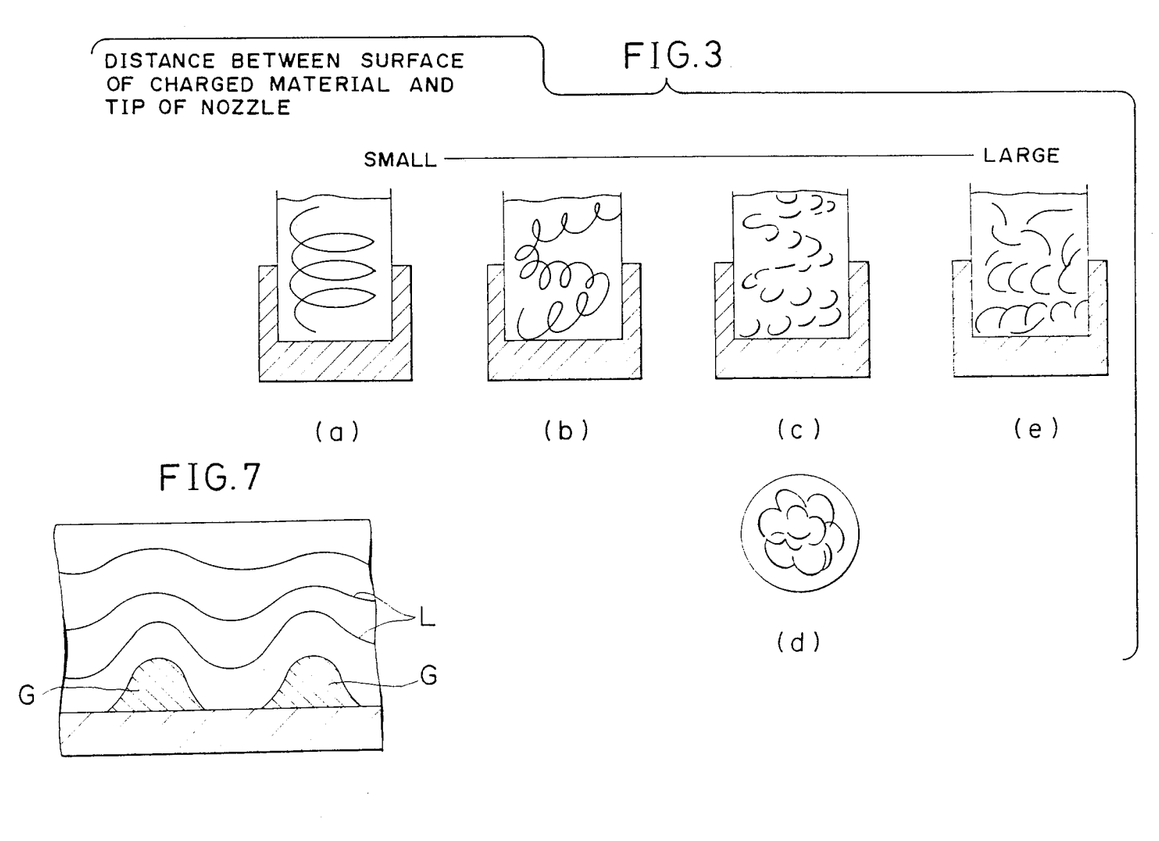
FIG. 7 is a drawing of a case in which a transparent gel base is charged before being charged to form a conical shape.

Similarly, during charging of the cosmetic material by rotation of the vessel, if the transparent gel base is first charged in a conical form at given distances on the bottom of the vessel 16, as shown in FIG. 7, and the transparent gel base containing the coloring material is then charged, the lines L which form the coil-shaped pattern formed by the coloring material are affected by the transparent gel base G which has a conical shape and was previously charged so as to have a waveform.

Examples of the present invention are described below in reference to the drawings.

Each of the examples comprises the multiple charging nozzle 3, the vessel holder 15 which is provided below the multiple charging nozzle 3 so as to be rotatable and movable in the longitudinal direction so that the transparent gel base and a liquid of the coloring material are charged from the multiple charging nozzle 3 while the vessel 16 being first raised and then rotated, as well as being downwardly moved.

(EXAMPLE 1)

Ratio between the two liquids charged;
transparent gel base : coloring material =98.5 : 1.5 (by weight)

The transparent gel base comprised 65% of glycerin, 1% of carboxyvinyl polymer, 1% of propylene glycol and 33% of water by weight and had a viscosity of 50,000 CP.

The coloring material comprised a liquid crystal.
Internal diameter of the tip of the charging nozzle; $\phi 10.5$ mm
Internal diameter of the tip of the sub-nozzle; $\phi 1.0$ mm
Charging time; 6.5 sec
Charging speed (charging amount/sec); constant
Lowering stroke of the vessel; 20 mm
Lowering speed of the vessel during charging; constant
Distance between the tip of the nozzle and the inner bottom of the vessel when the vessel was at the highest position; 3.5 mm
Rotational speed of the vessel; 80 rpm
Internal dimensions of the vessel; diameter, $\phi 35$ mm; height, 25 mm.

Figures 8A, 8B:
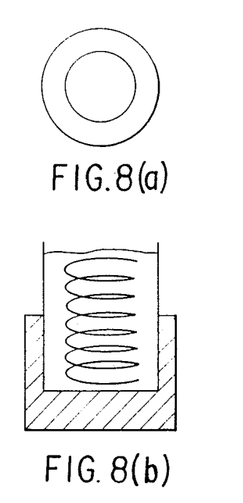

The results obtained are shown in FIGS. 8(a) and 8(b).

(EXAMPLE 2)

In this example, the conditions were the same as those used in Example 1 with the following exception
Charging time; 6.5 sec
Charging speed (charging amount/sec); sine curve (the charging speed was first low, high at an intermediate point and finally again low)

Figures 9A, 9B:
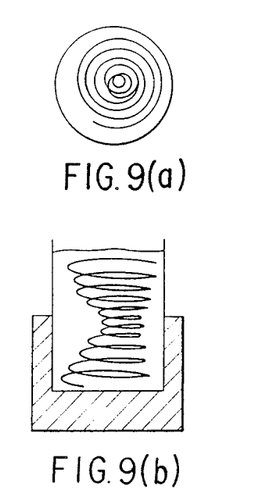

The results obtained are shown in FIGS. 9(a) and 9(b).

(EXAMPLE 3)

Figures 10A, 10B:
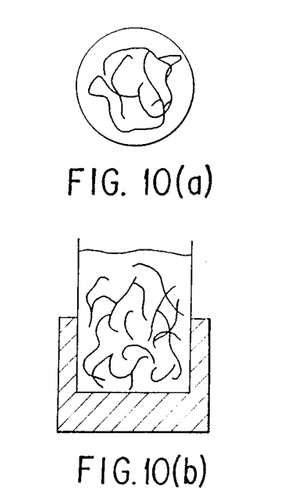

In this example, the conditions were the same as those used in Example 1 with the following exception
Lowering stroke of the vessel; 0 mm (the vessel was fixed during charging)
Distance between the tip of the nozzle and the inner bottom of the vessel when the vessel was at the highest position; 25.0 mm
Rotational speed of the vessel; 300 rpm The results obtained are shown in FIGS. 10(a) and 10(b).

(EXAMPLE 4)

Figures 11A, 11B:
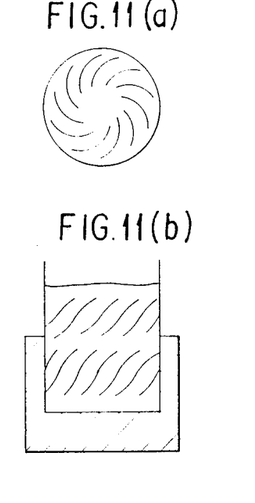

In this example, the conditions were the same as those used in Example 1 with the following exception:
Distance between the tip of the nozzle and the inner bottom of the vessel when the vessel was at the highest position; 6.5 mm
Rotational speed of the vessel; 300 rpm The results obtained are shown in FIGS. 11(a) and (b).

(EXAMPLE 5)

Ratio between the two liquid charged;
transparent gel base : coloring material =98.5 : 1.5 (by weight)

The transparent gel base was the same as in Example 1

The coloring material comprised pigment.

Internal diameter of the tip of the charging nozzle; $\phi 6.5$ mm,
Internal diameter of the sub-nozzle; $\phi 1.0$ mm
Charging time; 6 sec
Charging speed (charging amount/sec); constant
Lowering stroke of the vessel; 45 mm
Lowering speed of the vessel during charging; constant
Distance between the tip of the nozzle and the inner bottom of the vessel when the vessel was at the highest position; 3.5 mm
Rotational speed of the vessel; 560 rpm
Internal dimensions of the vessel; diameter, #25 mm height, 45 mm.

Figures 12A, 12B:
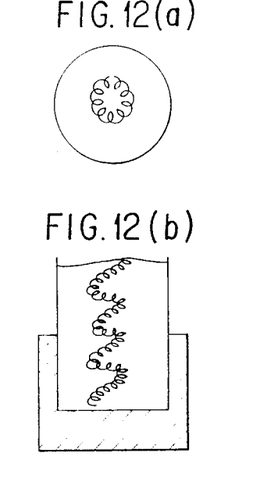

The results obtained are shown in FIGS. 12(a) and (b).

(EXAMPLE 6)

In this example, the conditions were the same as those used in Example 5 with the following exception:
Distance between the tip of the nozzle and the inner bottom of the vessel when the vessel was at the highest position; 5.0 mm
Internal dimensions of the vessel; diameter, $\phi 20$ mm height, 60 mm.

Figures 13A, 13B:
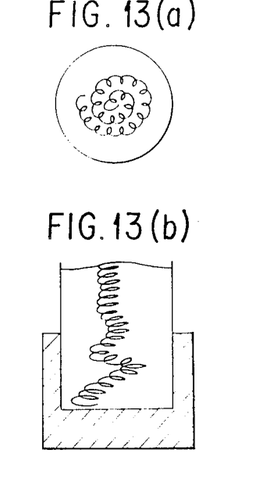

The results obtained are shown in FIGS. 13(a) and (b).

(EXAMPLE 7)

In this example, a cosmetic material was charged in a tube-shaped vessel.
Ratio between the two liquid charged;
transparent gel base : coloring material =9 : 1 (by weight)

The transparent gel base was the same as in Example 1.

Figures 14A, 14B:
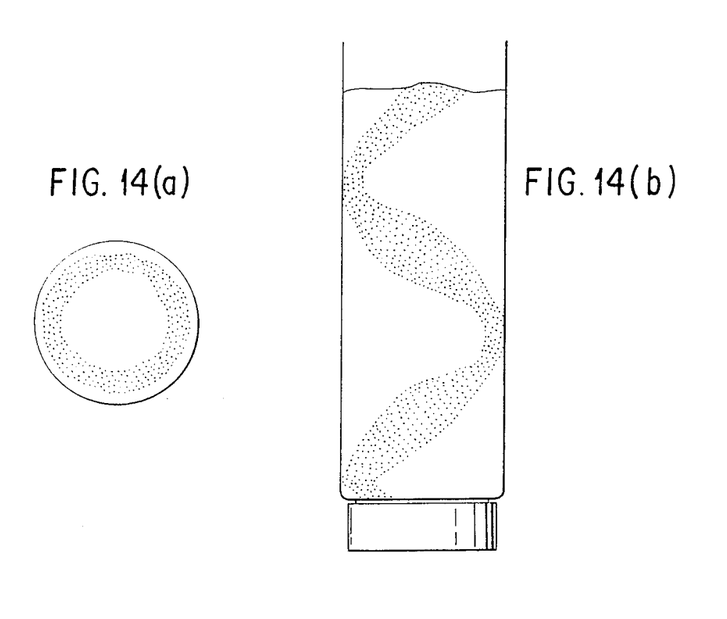

The coloring material comprised a mixture of the transparent gel base (the same as that used in Example 1) and pigment in a ratio of 10 : 1 (by weight).
Internal diameter of the tip of the nozzle; $\phi 10.5$ mm
Internal diameter of the tip of the sub-nozzle; $\phi 4.0$ mm
Charging time; 6 sec
Charging speed (charging amount/sec); constant
Lowering stroke of the vessel; 90 mm
Lowering speed of the vessel during charging; constant
Distance between the tip of the nozzle and the inner bottom of the vessel when the vessel was at the highest position; 5 mm
Rotational speed of the vessel; 9 rpm
Internal dimensions of the vessel; diameter, $\phi 30$ mm height, 104 mm The results obtained are shown in FIGS. 14(a) and 14(b).

(EXAMPLE 8)

Ratio between the two liquid charged;
transparent gel base : coloring material =99 : 1 (by weight)

The transparent gel base was the same as in Example 1.

The coloring material comprised an emulsion (water-in-oil type emulsion).
Internal diameter of the tip of the nozzle; $\phi 5.0$ mm
Internal diameter of the tip of the sub-nozzle; $\phi 1.0$ mm
Charging time; 6.5 sec
Charging speed (charging amount/sec); constant
Lowering stroke of the vessel; 50 mm
Lowering speed of the vessel during charging; constant Distance between the tip of the nozzle and the inner bottom of the vessel when the vessel was at the highest position; 4.0 mm
Rotational speed of the vessel; 620 rpm
Internal dimensions of the vessel; diameter, φ20 mm height, 55 mm
The results obtained are shown in FIGS. 12(*a*) and 12(*b*).

(EXAMPLE 9)

Ratio between the two liquid charged;
transparent gel base : coloring material =97 : 3 (by weight)
The transparent gel base was the same as in Example 1.
The coloring material comprised a mixture of the transparent gel base and an emulsion (water-in-oil type emulsion) in a ratio of 2 : 1 and had a milky color.
Internal diameter of the tip of the nozzle; φ4.0 mm
Internal diameter of the tip of the sub-nozzle; φ1.0 mm
Charging time; 4.0 sec
Charging speed (charging amount/sec); constant
Lowering stroke of the vessel; 20 mm
Lowering speed of the vessel during charging; constant
Distance between the tip of the nozzle and the inner bottom of the vessel when the vessel was at the highest position; 4.0 mm
Rotational speed of the vessel; 620 rpm
Internal dimensions of the vessel; diameter, φ12 mm height, 25 mm
The results obtained are the same as those shown in FIGS. 12(*a*) and 12(*b*).

The present invention enables any three-dimensional pattern to be formed in a transparent cosmetic material and a cosmetic material containing a beautiful pattern to be easily produced in accordance with the demands of consumers.

COLLATION LIST BETWEEN A COLOR NUMBER AND A PIGMENT NAME

The color numbers described in this specification are based on the law number in Japanese Cosmetics and Medical Instruments Act. They are corresponding to the following chemical compounds and Food, Drugs and Cosmetics Color number or Drugs and Cosmetics Color number in U.S.A.

| Color No. in Japan | pigment name | F.D. & C. or D. & C. |
|---|---|---|
| Red No. 2 | Amaranth | F.D. & C. Red No. 2 |

| Red No. 204 | Lake red CBA | D. & C. Red No. 9 |
|---|---|---|

| Red No. 205 | Lithol red | D. & C. Red No. 1 |
|---|---|---|

| Red No. 219 | Brilliant Lake red R | D. & C. Red No. 31 |
|---|---|---|

| Color No. in Japan | pigment name | F.D. & C. or D. & C. |
|---|---|---|
| |  | |
| Blue No. 1 | Brilliant blue FCF | F.D. & C. Blue No. 1 |
| |  | |
| Yellow No. 4 | Tartrazine | F.D. & C. Yellow No. 5 |
| |  | |
| Yellow No. 204 | Quinoline yellow SS | D. & C. Yellow No. 11 |
| |  | |

What is claimed is:

1. A method of charging a transparent cosmetic material containing a three-dimensional pattern in which a coloring material is charged at the same time as a transparent gel base comprising a water-soluble polymer or inorganic gelatinizer is charged into a vessel so as to form a three-dimensional pattern in said transparent gel base, the method comprising:
   charging said transparent gel base into a charging nozzle from a first supply source of said transparent gel base, as well as joining said coloring material charged from a second supply source thereof to said transparent gel base insaid charging nozzle; and receiving said transparent gel base and said coloring material which are injected from a tip of said charging nozzle by a vessel, said charging nozzle and said vessel having longitudinal axes which are substantially parallel to each other and define a Z-axis;
   said charging being performed by rotating said vessel in an XY plane, as well as moving at least one of said vessel and said charging nozzle away from each other along the Z-axis when said transparent gel base and said coloring matering which are injected from said tip of said charging nozzle are received by said vessel;
   said tip of said charging nozzle being positioned above the surface of said cosmetic material in the vessel during said charging, whereby said coloring material forms a three-dimensional pattern which is visible inside of said transparent gel base.

2. A method of charging a transparent cosmetic material containing a three-dimensional pattern according to claim 1, wherein said charging is performed by rotating said vessel in the XY plane, as well as moving at least one of said vessel and said charting nozzle in the Z-axis direction so that said vessel and charging nozzle do not contact each other when said transparent gel base and said coloring material which are injected from said tip of said charging nozzle are received by said vessel.

3. A method of charging a transparent cosmetic material containing a three-dimensional pattern according to claim 1, wherein said sub-nozzle forms said pattern in said transparent gel base spaced from an outer periphery of the gel base in the vessel.

4. An apparatus for charging transparent cosmetic material containing a three-dimensional comprising a multiple charging nozzle which has a main charging nozzle for supplying a transparent gel base from a first charger and at least one sub-nozzle that serves to supply a coloring material from a second charger and that is contained in said main charging nozzle; and a vessel holder which serves to hold a vessel and is rotatable and which is provided below said multiple charging nozzle, said vessel holder and main charging nozzle having longitudinal axes which are substantially parallel to each other and define a Z-axis; one or both of said vessel holder and multiple charging nozzle being movable in longitudinal directions by a driving apparatus, said driving apparatus positioning a tip of said main charging nozzle above the surface of the cosmetic material in the vessel during charging; and said at least one sub-nozzle having an output end which is disposed eccentrically to the longitudinal axis of said charging nozzle, whereby said sub-nozzle forms a three-dimensional pattern which is visible inside of said transparent gel base.

5. An apparatus for charging a transparent cosmetic material containing a three-dimensional pattern according to claim 4, wherein said driving, apparatus comprises a longitudinal driving means for longitudinally moving said vessel holder and a rotational driving means for rotating said vessel holder.

6. An apparatus for charging a transparent cosmetic material containing a three-dimensional pattern according to claim 4 wherein the multiple charging nozzle is rotatable.

7. An apparatus for charging a transparent cosmetic material containing a three-dimensional pattern according to claim 4, wherein said at least one sub-nozzle forms said pattern in said gel base spaced from an outer periphery of the gel base in the vessel.

* * * * *